United States Patent [19]
Vercauteren et al.

[11] Patent Number: 5,962,276
[45] Date of Patent: Oct. 5, 1999

[54] PURIFIED ACID-STABLE ALPHA-AMYLASE FROM FUNGAL ORIGIN

[75] Inventors: Ronny Vercauteren, Beveren; Els Ginelle Alexander Dendooven, Strombeek-Bever; An Amanda Jules Heylen, Vilvoorde, all of Belgium

[73] Assignee: Cerestar Hold B.V., LA Saas van Gent, Netherlands

[21] Appl. No.: 09/024,579

[22] Filed: Feb. 17, 1998

[30] Foreign Application Priority Data

Feb. 21, 1997 [GB] United Kingdom .................... 9703641

[51] Int. Cl.$^6$ .............................. C12P 19/14; C12N 9/99; C12N 9/28; C12N 9/30
[52] U.S. Cl. ........................... 435/99; 435/184; 435/202; 435/203; 435/256.1; 435/914; 435/917
[58] Field of Search ..................................... 435/203, 202, 435/184, 256.1, 914, 917, 99

[56] References Cited

U.S. PATENT DOCUMENTS 3,416,997  12/1968  Barton .
4,284,722   8/1981  Tamuri et al. .

FOREIGN PATENT DOCUMENTS 138 428   4/1985  European Pat. Off. .
157 638  10/1985  European Pat. Off. .
27 35 480  2/1978  Germany .

OTHER PUBLICATIONS

Hayashida, Agr. Biol. Chem. 39(11):2093–2099, 1975.
Chemical Abstracts, vol. 89, No. 11, Sep. 11, 1978, Abstract No. 86325, Mahmoud, S.A.Z. et al "Isolation and Purification of Glucoamylase From a Submerged Culture of *Aspergillus foetidus* ATCC 14916".
Database WPI, Section Ch.Week 8804, Derwent Publication Ltd.,London, Sep. 21, 1987.

*Primary Examiner*—Francisco Prats
*Attorney, Agent, or Firm*—Pillsbury Madison & Sutro Intellectual Property Group

[57] ABSTRACT

The present invention describes a simple and inexpensive purification method for acid-stable fungal alpha-amylase wherein the alpha-amylase is obtained without significant loss of enzyme activity. The purified acid-stable alpha-amylase which is obtained is substantially free from glucoamylase. The method for obtaining an acid-stable alpha-amylase comprises the steps of adjusting the pH of the enzyme containing solution to a value between 1 and 8, heating the solution to a temperature and for a time sufficient to inactivate glucoamylase, removing the denatured glucoamylase.

The purified acid-stable alpha-amylase is used for the conversion of starch. The purified alpha-amylase is also used in an immobilized form.

17 Claims, No Drawings

PURIFIED ACID-STABLE ALPHA-AMYLASE FROM FUNGAL ORIGIN

TECHNICAL FIELD

The present invention relates to a purified acid-stable fungal alpha-amylase and to a process for obtaining said purified alpha-amylase. Furthermore the use of the purified alpha-amylase in free and immobilized form for obtaining specific glucose syrups is demonstrated.

BACKGROUND OF THE INVENTION

Acid-stable alpha-amylases from fungal origin have been discovered a long time ago. For example, the acid-stable alpha-amylase from *A. niger* has been known for over 30 years (Y. Minoda, K. Yamada, Agr. Biol. Chem., 27(11), 806–811(1963)) and has been thoroughly characterised by Minoda, Yamada and co-workers. The same authors showed the stabilisation of the enzyme activity in the presence of $Ca^{2+}$. The presence of an acid-unstable alpha-amylase in the *Aspergillus niger* preparations was disclosed by the same authors. The acid-stable alpha-amylase enzyme has a pH optimum between 3 and 4 and the optimal temperature is in the range of 70 to 75° C.

Several procedures have been developed for obtaining acid-stable alpha-amylase in purified form. One method (Minoda and Yamada, cited above) uses fractional precipitation with ammonium sulfate, rivanol and acetone to obtain the enzyme in crystalline form. It was found that this crystalline alpha-amylase was contaminated with an acid-unstable alpha-amylase, whereas glucoamylase and transglucosidase were found to be removed. The acid-unstable alpha-amylase could subsequently be removed by treatment of the alpha-amylase mixture at acidic pH (pH 2.5) and 37° C., followed by fractionation. A further purification was performed by recrystallisation with acetone and gelfiltration with Sephadex G-50.

Other publications describe a purification method based on chromatography on DEAE-Sephadex A-25 (D. S. Chong, Y. Tsujisaka, *J. Fennent. Technol*, 54(4), 264–266(1976)) or ammonium sulfate precipitation followed by chromatography on DEAE-Sephadex A-50 (N. Ramasesh, K. R. Sreekantiah, V. S. Murthy, *Starch*, 34(8), 274–279(1982)). Also Sephadex G-25, followed by Sepharose Q Fast Flow chromatography has been utilised (Y-Y. Linko, X. Y. Wu, *Biotechnology Techniques*, 7(8)).

European patent application EP 0138 428 describes the production of an alpha-amylase which is free from transferase and amyloglucosidase. This is achieved by treating suitable *Aspergillus niger* with mutagenic agents and selecting mutant strains which do not produce the undesired enzyme activities. The fermentation broth of these mutant strains then mainly contains the acid-stable alpha-amylase activity.

The dextrinisation and saccharification properties of the acid-stable alpha-amylase from *A. niger* have been extensively reported. The conversion of liquefied starch into glucose using a blend of glucoamylase and acid-stable alpha-amylase is described in European patent application 0,140,410 where it is shown that the presence of acid-stable alpha-amylase shortens the saccharification time and gives higher dextrose yields. Also the paper of Linko et al.(cit. above) describes the use of acid-stable alpha-amylase in the production of dextrose.

Hansen (T. T. Hansen, *New Approaches to Research on Cereal Carbohydrates*, eds. R. D Hill and L. Munck, Elsevier Science Publishers B. V., Amsterdam 1985, 211–216) has reported the use of acid-stable alpha-amylase for the saccharification of a 12 DE maltodextrin, to obtain a syrup with 7% glucose, 48% DP2, 26% DP3 and 20% DP4+ after 96 hours. The production of a 63 DE syrup out of a 42 DE acid liquefied syrup by an immobilized acid-stable alpha-amylase has been described in the same paper. This paper however does not describe how the acid-stable alpha-amylase which is used was purified. DE (dextrose equivalent) is a measure for the number of reducing groups which are present in the molecules. Pure glucose has a DE of 100 and undegraded starch has a DE of 0. Liquefaction of starch with the acid-stable alpha-amylase at 75–85° C. gave starch substrates, which were saccharified by glucoamylase. The obtained syrups had the correct dextrose yield, but were starch positive and had poor filterabilities. The use of immobilised acid-stable alpha-amylase obtained from mutant strains has been described in European patent application EP 0,157,638.

With the potential to be used as a post-liquefaction enzyme for high maltose production where a low initial DE is required, a starch slurry pre-liquefied with *B. Iicheniformis* alpha-amylase was subjected to incubation with acid-stable alpha-amylase at 90° C. and pH 5. After 20 minutes the temperature was lowered to 60° C. and barley beta-amylase together with pullulanase was added. The final syrup contained 0.5% glucose and 71% maltose and 91% fermentable sugars. A reference syrup produced without alpha-amylase had the same DP1 and DP2 composition, but only 77% fermentable sugars.

An acid-stable alpha-amylase from *A. niger* able to degrade raw starch has been described (B. N. Okolo, L. I. Ezeogu, C. N. Mba, *J. Sci. Food. Agric.*, 69,109–115 (1995)). Acid-stable alpha-amylases can not only be found in *Aspergillus niger*, also in *Aspergillus awamori* acid stable alpha-amylases have been found (R. S. Bhella, I. Altosaar, Can. J. Microbiol., 31, 149–153(1985)) these alpha-amylases were reported to be stable between pH 3.5 and 6.5.

Although it is apparent from the mentioned literature that the acid-stable alpha-amylase from *Aspergillus niger*, or from other Aspergillus species, which produce acid-stable alpha-amylase, is of potential industrial significance, no commercial Aspergillus sp. acid-stable alpha-amylase preparation is free of glucoamylase side activity. The presence of the glucoamylase in the cornmercial acid-stable alpha-amylase preparations significantly reduces the range of applications where these preparations can be utilized.

SUMMARY OF THE INVENTION

The present invention describes a simple and inexpensive purification method for acid-stable fungal alpha-amylase wherein the alpha-amylase is obtained without significant loss of enzyme activity.

The present invention discloses a purified acid-stable alpha-amylase which is substantially free of glucoamylase. Preferably, the alpha-amylase is of fungal origin, wherein the preferred fungus is an Aspergillus species, preferably *Aspergillus niger* or *Aspergillus awamori*.

The present invention also discloses a method for obtaining an acid-stable alpha-amylase comprising the steps of
   adjusting the pH of the enzyme-containing solution to a value between 1 and 8,
   heating the solution to a specific temperature and for a time sufficient to inactivate glucoamylase,
   removing the denatured glucoamylase.

In a preferred embodiment of the invention the heating is performed in the presence of calcium ions. The heating is to a temperature of between 40 and 80° C. preferably between 50 and 75° C.

The present invention further discloses the use of a purified acid-stable alpha-amylase for the conversion of starch. The purified enzyme of the present invention is used to prepare high maltose syrups or high maltotriose syrups containing low amounts of glucose that is less than 10% preferably less than 5%. The purified alpha-amylase is also used in an immobilized form.

DETAILED DESCRIPTION OF THE INVENTION

The present invention describes a thermal treatment of alpha-amylase/glucoamylase containing culture broth obtained after growth of a fungus preferably of an Aspergillus sp. at specific pH values. The pH and temperature are chosen to reduce or eliminate the glucoamylase activity in these preparations. The deactivated glucoamylase flocculates after this treatment and can be easily filtered off or removed by centrifugation or another separation technique, thereby yielding a pure acid-stable alpha-amylase preparation. The acid-stable alpha-amylase so-obtained can be used as such or after concentration and addition of stabilising agents.

Since also the acid-unstable alpha-amylase activity is destroyed during this thermal treatment, a solution containing only acid-stable alpha-amylase is obtained and which is free of glucoamylase, acid-unstable alpha-amylase and transglucosidase. The solution can be used as such or it can be concentrated before use by filtration, heating or freeze-drying. Stabilising agents are added if necessary.

The present invention discloses a purified acid-stable alpha-amylase which is substantially free from glucoamylase. Preferably the alpha-amylase is of fungal origin, wherein the fungus is an Aspergillus species, preferably *Asergillus niger* or *Asmergillus awamon*.

The present invention also discloses a method for obtaining an acid-stable alpha-amylase comprising the steps of
adjusting the pH of the enzyme-containing solution to value between 1 and 8,
heating the solution to a specific temperature and for a time sufficient to inactivate glucoamylase,
removing the denatured glucoamylase.

In a preferred embodiment of the invention the enzyme-containing solution is a fermentation broth. The cellular or microbial material is first removed for example by filtration or centrifugation. The fermentation broth is then heated. The heating is to a temperature wherein the glucoamylase is inactivated whereas at the same time acid-stable alpha-amylase keeps its activity. The exact temperature depends on the source of the enzyme and the composition of the fermentation broth. Temperatures between 50 and 80° C. have been used, but preferred temperatures are in the range of from 60 to 75° C. When the temperature is too high this will influence the residual activity of the acid-stable alpha-amylase so care should be taken not to overheat the preparation. Preferably the heating is performed in the presence of calcium ions. The calcium ions should be present in an amount which is sufficient to stabilise the acid-stable alpha-amylase. Amounts of calcium ions in the range of between 50 and 350 ppm have been satisfactorily used. The exact amounts may depend on the source of the enzyme and possible contaminants in the fermentation broth. Values of between 150 and 250 ppm have been found to be particularly useful.

It is also possible to use the present method on enzyme preparations as supplied by enzyme suppliers as these contain a considerable amount of glucoamylase. In this case it is clear that the method of the present invention does not start with the fermentation broth but with the enzyme preparation as supplied by the manufacturer from which the microbial material has already been removed and which is generally buffered and contains stabilising agents. These preparations also contain the enzymes in a much more concentrated form.

The present invention further discloses the use of a purified acid-stable alpha-amylase for the conversion of starch. With the purified enzyme it becomes possible to prepare high maltose syrups containing relatively low amounts of glucose that is the amount of glucose is lower than 10% preferably lower than 5%.

The purified alpha-amylase may be used as such or it may be used in an immobilized form. The immobilisation may be performed with known immobilising techniques. The enzyme may for example be entrapped in a matrix or gel (alginate, carrageenan) or it may be bound to ion exchange resins.

Commercially available alpha-amylase products are found to contain a considerable amount of enzymatic contamination. Specifically, acid-stable alpha-amylase preparations obtained from fungal origin are found to contain considerable glucoamylase and acid-unstable alpha-amylase activities.

The starting enzyme for Examples 1, 2 and 5 (available from Stern Enzyme) was found to contain 7.2 GAU/g and 4500 AAU/g. A further preparation sold as G-ZYME™ G998 by Enzyme Bio-Systems (used in Examples 3 and 4) contained 15.7 GAU/g and 840 AAU/g. Other enzyme preparations which have been investigated were SANACTASE (powder, Meiji Seika Kaishi Ltd) 1380 AAU/g and 123 GAU/g and MULTIFRESH (spray-dried variant of G998, Enzyme Bio-Systems) 119 GAU/g and 9356 AAU/g.

In Example 1 it is demonstrated that incubation at 70° C. for 1 hour in the presence of calcium ions gives complete inactivation of glucoamylase whereas 74% of the acid-stable alpha-amylase activity remains. At 65° C. residual activity of alpha-amylase is about 10% higher however also glucoamylase is not fully inactivated as demonstrated in Example 2. Example 3 confirms the result of Example 1 for a second enzyme preparation. When no calcium ions are added to the preparation of Example 4 the activity of the alpha-amylase diminishes very strongly.

In Example 5 it is demonstrated that the pH influences the speed and amount of inactivation of the alpha-amylase and glucoamylase. In Example 6 the amount of acid-unstable alpha-amylase is determined in the G-ZYME enzyme preparation.

Example 7 demonstrates that the purified acid-stable alpha-amylase is used to obtain high maltose syrups or even high maltotriose syrups containing less than 10% glucose preferably less than 5%. This is not possible with the commercially available enzyme preparations.

Example 8 shows that it is possible to obtain 62 DE syrup starting from a 42 DE syrup when the purified acid-stable alpha-amylase is used in an immobilised form.

EXAMPLES

Determination of enzyme activities is by standard methods.

Generally as provided by the enzyme supplier.

Glucoamylase activity is determined by hydrolysis of para-nitrophenyl-alpha-D-glucopyranoside (K. A. Holm,

*Analyst*, 3, 927–929 (1986)). Basically, the procedure is as follows. An enzyme preparation is allowed to react under standard conditions (pH 4.2, 55° C.) with para-nitrophenyl-alpha-D-glucopyranoside. In the presence of a glucoamylase this substrate is degraded to glucose and para-nitrophenolate which has a yellow color. The amount of para-nitrophenolate produced is determined colorimetrically. Enzyme activity is calculated from a standard curve expressing the relation between the concentration of para-nitrophenolate and the absorbance.

Alpha-amylase activity is determined by reacting the enzyme with a standard starch solution. The amount of alpha-amylase activity is measured by the rate at which the iodine-staining capacity of the starch is decreased (G. B. Manning, L. L. Campbell, *J. Biological Chemistry*, 236, 2952–2957 (1961)).

EXAMPLE 1

1 g of an alpha-amylase/glucoamylase containing powder (4500 AAU/g, 7.2 GAU/g, 200 mg protein/g powder), from Stern Enzyme, was dissolved in 19 g 0.05 N NaAc/HAc (Ac=acetate) buffer of pH 4.2 containing 200 ppm of $Ca^{2+}$. After filtration to obtain a clear liquid the solution was incubated at 70° C. during a certain time. At regular intervals the heat treatment was stopped by adding 1 ml samples of the incubated solution to 9 ml of a 0.05 N NaAc/HAc buffer at pH 5 and ambient temperature. The activities of GA and AA in these solutions were determined. The results are shown in the table. Typically the protein content of the remaining acid-stable alpha-amylase was only 20% of the original protein content.

| Incubaton time (h) | % total AA activity * remaining | % GA activity remaining |
| --- | --- | --- |
| 0.5 | 77 | 0.015 |
| 1 | 74 | 0 |
| 1.5 | 64 | 0 |
| 2.0 | 50 | 0 |
| 3.0 | 40 | 0 |
| 4.4 | 25 | 0 |

* total AA (alpha-amylase) activity = sum of activities of acid-stable and acid-unstable alpha-amylases.

It is clearly demonstrated that after a short incubation at pH 4.2 and 70° C. all of the glucoamylase activity is destroyed.

EXAMPLE 2

1 g of an alpha-amylase/glucoamylase containing powder (4500 AAU/g, 7.2 GAU/g, 200 mg protein/g powder), from Stern Enzyme, was dissolved in 19 g 0.05 N NaAc/HAc buffer of pH 3.5 containing 200 ppm of $Ca^{2+}$. After filtration to obtain a clear liquid the solution was incubated at 65° C. during a certain time. At regular intervals the heat treatment was stopped by filtration of 1 ml samples of the incubated solution and subsequent addition to 9 ml of a 0.05 N NaAc/HAc buffer at pH 5 and ambient temperature. The activities of GA and AA in these solutions were determined. The results are shown in the table. Typically the protein content of the remaining acid-stable alpha-amylase was only 20% of the original protein content.

| Incubaton time (h) | % total AA activity* remaining | % GA activity remaining |
| --- | --- | --- |
| 0.7 | 100 | 16 |
| 1.1 | 88 | 16 |
| 1.6 | 88 | 14 |
| 2.1 | 90 | 8.2 |
| 2.5 | 90 | 8.6 |
| 3.0 | 82 | 8.1 |
| 3.5 | 84 | 8.9 |

*total AA activity = sum of activities of acid-stable and acid-unstable alpha-amylases.

It is clearly demonstrated that the incubation at pH 3.5 and 65° C. diminishes most of the glucoamylase activity.

EXAMPLE 3

1 g of G998 (a commercial liquid acid-stable amylase/glucoamylase preparation from Enzyme Bio-Systems, 15.7 GAU/g, 840 AAU/g, 38 mg proteins/g enzyme solution) was dissolved in 19 g 0.05 N NaAc/HAc buffer of pH 3.5 containing 200 ppm of $Ca^{2+}$. After filtration to obtain a clear liquid the solution was incubated at 65° C. during a certain time. At regular intervals the heat treatment was stopped by adding 1 ml samples of the incubated solution to 9 ml of a 0.05 N NaAc/HAc buffer at pH 5 and ambient temperature. The activities of GA and AA in these solution were determined. The results are shown in the table. Typically the protein content of the remaining acid-stable alpha-amylase was only 20–25% of the original protein content.

| Incubaton time (h) | % total AA activity * remaining | % GA activity remaining |
| --- | --- | --- |
| 0.7 | 98 | 6.2 |
| 1 | 97 | 1.4 |
| 1.5 | 80 | 1.1 |
| 2 | 75 | 0.2 |
| 2.5 | 76 | 0.0 |
| 3.5 | 76 | 0.0 |

* total AA activity = sum of activities of acid-stable and acid unstable alpha-amylases.

Also in this example the acid-stable alpha-amylase is easily liberated from contaminating glucoamylase activity.

EXAMPLE 4

The experimental conditions used in example 4 are the same as those described in example 3, except that no $Ca^{2+}$ was added to the NaAc/HAc buffer at pH 3.5.

| Incubation time (min) | % total AA activity * remaining without $Ca^{2+}$ | % total AA activity remaining with Ca2+ |
| --- | --- | --- |
| 10 | 49 | |
| 20 | 32 | |
| 30 | 29 | |
| 40 | 21 | 98 |

* total AA activity = sum of activities of acid-stable and acid unstable alpha-amylases.

From these figures it is clear that the presence of $Ca^{2+}$ is necessary to increase the thermal stability of the acid-stable alpha-amylase.

EXAMPLE 5

0.5 g of an alpha-amylase/glucoamylase containing powder (4500 AAU/g, 7.2 GAU/g, 200 mg protein/g powder), from Stern Enzyme, was dissolved in 2.5 ml demineralised water. After filtration to obtain a clear liquid, a desalting step on A PD-10 column (Pharmacia) was performed, yielding 3.5 ml of alpha-amylase/glucoamylase containing solution. This solution was diluted four times with 0.1 N NaAc/HAc buffer of pH 4.2 or 3.5 containing 200 ppm of $Ca^{2+}$. The so prepared solutions were incubated at 70° C. during a certain time. After regular intervals the heat treatment was stopped by adding 1 ml samples of the incubated solutions to 9 ml of a 0.05 N NaAc/HAc buffer at pH 5 and ambient temperature. The activities of GA and AA in these solutions were determined. The results are shown in the table. Typically the protein content of the remaining acid-stable alpha-amylase was only 20% of the original protein content.

| PH | Incubation time (h) | % total AA activity * remaining | % total GA activity remaining |
|---|---|---|---|
| 3.5 | 0.08 | 84 | 0 |
| 4.2 | 0.17 | 100 | 55 |
| 4.2 | 0.25 | 80 | 10 |

* total AA activity = sum of activities of acid-stable and acid-unstable alpha-amylases.

EXAMPLE 6

Determination of the amount of acid-unstable alpha-amylase.

To establish the amount of acid-unstable alpha-amylase in a commercial Aspergillus sp. alpha-amylase preparation, following method was applied: a solution of the enzyme was brought to pH 2.5 and incubated at 37° C. for 30 minutes. Then it was cooled and neutralised to pH 4.8. Subsequently, the alpha-amylase activity was determined.

| Enzyme | % acid unstable alpha-amylase activity in original enzyme preparation |
|---|---|
| G998 | 5 |
| Stern enzyme | 8 |

Since the remaining relative AA activities are compared to the total AA activity in examples 1–5, this means that the remaining acid-stable alpha-amylase activity is higher than the values given in the table in examples 1–5.

EXAMPLE 7

A 5 DE (dextrose equivalents) spray-dried maltodextrin (C☆PUR 1904, made from corn through liquefaction with *Bacillus licheniformis* thermostable α-amylase) was saccharified with G998 or with the purified α-amylase obtained from G998 as described in example 3.

The saccharifications were carried out at 60° C. and pH 4.5, and at a substrate concentration of 30 g/100 g of solution.

In the case of the saccharification with G998, 0.1% on dry matter of G998 was added to the saccharification mixture. For the saccharification with the purified α-amylase, the same equivalent of α-amylase units as present in 0.1% d.s. G998 were added.

The following results were obtained:

| Enzyme | Saccharification time (hour) | $DP_1$ (%) | $DP_2$ (%) | $DP_3$ (%) | $DP_n$ (%) |
|---|---|---|---|---|---|
| G998 | 23.2 | 76.2 | 11.0 | 0.6 | 12.2 |
| G998 | 28.0 | 78.3 | 9.0 | 1.0 | 11.7 |
| G998 | 48.5 | 87.0 | 4.8 | 1.0 | 7.2 |
| G998 | 72.4 | 91.4 | 3.4 | 0.7 | 4.5 |
| pur. AAA* | 23.2 | 2.4 | 26.9 | 31.2 | 39.5 |
| pur. AAA* | 28.0 | 3.5 | 30.8 | 31.7 | 34.0 |
| pur. AAA* | 48.5 | 5.3 | 39.9 | 30.4 | 24.4 |
| pur. AAA* | 72.4 | 6.6 | 43.7 | 28.2 | 21.5 |

*Purified acid stable α-amylase, obtained according to method 3.

From this table, it is evident that the purified α-amylase produces a totally different product spectrum than the original G998, which is an mixture of α-amylase and glucoamylase activities. Using the purified alpha-amylase of the present invention it is possible to obtain maltose (DP2) syrups containing low amounts of glucose (DP1). The amount of glucose is below 10%.

EXAMPLE 8

8900 AAU of G998 was brought into contact with 10 ml of a wet ion exchanger. The mixture was stirred for 12 h at ambient temperature, and then washed with demineralised water. The conjugate was put into a thernostated glass column equipped with a double jacket and a 42 DE syrup, brought at pH 4.5, was run through it at 50° C.

Another conjugate was made by offering 8900 U of purified α-amylase, as obtained in example 3, to 10 ml the same wet ion exchanger as used for G998 immobilisation. The mixture was stirred for 12 h at ambient temperature, and then washed with demineralised water. The conjugate was put into a thermostated glass column equipped with a double jacket and a 42 DE syrup, brought at pH 4.5, was run through it at 50° C.

The aim was to produce a 62 DE syrup. The following results were obtained:

| Conjugate | Flow rate*** (BV/h) | $DP_1$(%) | DP2(%) | $DP_3$(%) | $DP_4$(%) | $DP_n$(%) | D.E.**** |
|---|---|---|---|---|---|---|---|
| SUBSTRATE (42DE) | not applicable | 20.3 | 14.6 | 13.1 | 9.9 | 42.1 | 44.5 |
| imm. G998* | 2.2 | 91.6 | 8.7 | 3.4 | 2.3 | 3.9 | 89.4 |
| imm. G998* | 3.5 | 82.1 | 7.1 | 3.6 | 2.3 | 4.9 | 89.2 |
| imm. G998* | 5.1 | 80.7 | 6.7 | 3.8 | 2.4 | 6.4 | 88.0 |
| imm. G998* | 5.5 | 78.7 | 7.4 | 4.3 | 2.6 | 7.0 | 86.7 |
| imm. pur. AA** | 2.2 | 34.0 | 35.1 | 14.2 | 6.2 | 10.3 | 62.9 |
| imm. pur. AA** | 2.5 | 32.3 | 34.5 | 15.8 | 6.0 | 11.3 | 62.0 |
| imm. pur. AA** | 3.7 | 29.7 | 34.1 | 17.4 | 6.1 | 12.5 | 59.7 |

-continued

| Conjugate | Flow rate*** (BV/h) | DP$_1$(%) | DP2(%) | DP$_3$(%) | DP$_4$(%) | DP$_n$(%) | D.E.**** |
|---|---|---|---|---|---|---|---|
| imm. pur. AA** | 5.2 | 27.8 | 33.1 | 19.1 | 6.1 | 13.8 | 58.1 |

*immobilised G998 conjugate
**immobilised purified acid-stable α-amylase conjugate, purified according to example 3.
***bed volumes/hour
****dextrose equivalent From the table it is directly evident that the action pattern of the immobilised purified acid-stable α-amylase from G998 is totally different from the action pattern given by immobilised G998.

We claim:

1. A method for obtaining a purified acid-stable alpha-amylase from fungal origin comprising:
   adjusting the pH of an enzyme-containing solution to a pH value between 1 and 8, the enzyme-containing solution containing an acid-stable alpha-amylase and gluco-amylase,
   heating the enzyme-containing solution for a time and at a temperature sufficient to inactivate the gluco-amylase, and
   obtaining a purified acid-stable alpha-amylase preparation.

2. The method according to claim 1, wherein obtaining the purified acid-stable alpha-amylase preparation includes removing deactivated gluco-amylase from the heated solution.

3. A method according to claim 1, wherein the pH is adjusted to an acidic pH value.

4. A method according to claim 1, wherein the pH is adjusted to a value below 4.2.

5. A method according to claim 1, wherein during said heating the enzyme-containing solution is between 40° C. and 80° C.

6. A method according to claim 1, wherein during said heating the enzyme-containing solutionis between 50° C. and 75° C.

7. A method according to claim 1, wherein the enzyme-containing solution comprises a fermentation broth.

8. A method according to claim 1, wherein said heating is conducted in the presence of calcium ions.

9. A method according to claim 8, wherein the calcium ions are present in an amount in the range of 50 ppm to 350 ppm.

10. A method according to claim 8, wherein said heating is conducted in the presence of 150 to 250 ppm of calcium ions.

11. A method according to claim 1, wherein in said heating the temperature is greater than 65° C.

12. A method according to claim 1, wherein said enzyme-containing solution comprises a fermentation broth, said fermentation broth following fermentation in the presence of a fungus selected from the genera Aspergillus.

13. A method according to claim 11, wherein the fungus is *Aspergillus niger* or *Aspergillus awamori*.

14. A method for conversion of starch comprising heating said starch in the presence of a purified acid-stable alpha-amylase, wherein said purified acid-stable alpha-amylase is obtained by adjusting the pH of an enzyme-containing solution to a pH value between 1 and 8, the enzyme-containing solution containing an acid-stable alpha-amylase and gluco-amylase, heating the enzyme-containing solution for a time and at a temperature sufficient to inactivate the gluco-amylase, and obtaining a purified acid-stable alpha-amylase preparation.

15. A method for preparing high maltose syrups or high maltotriose syrups comprising treating a starch with a purified acid-stable alpha-amylase obtained by adjusting the pH of an enzyme-containing solution to a pH value between 1 and 8, the enzyme-containing solution containing an acid-stable alpha-amylase and gluco-amylase, heating the enzyme-containing solution for a time and at a temperature sufficient to inactivate the gluco-amylase, and obtaining a purified acid-stable alpha-amylase preparation, whereby a high maltose syrup or high maltotriose syrup containing less than 10% glucose is obtained.

16. A method according to claim 15, wherein said high maltose syrup or high maltotriose syrup contains less than 5% glucose.

17. A method according to claim 15, wherein the purified acid-stable alpha-amylase is immobilized.

* * * * *